(12) United States Patent
Honeyman

(10) Patent No.: US 12,228,537 B2
(45) Date of Patent: Feb. 18, 2025

(54) AGRICULTURAL MACHINES COMPRISING CAPACITIVE SENSORS, AND RELATED METHODS AND APPARATUS

(71) Applicant: AGCO Corporation, Duluth, GA (US)

(72) Inventor: Friedrich Robert Honeyman, Hesston, KS (US)

(73) Assignee: AGCO Corporation, Duluth, GA (US)

( * ) Notice: Subject to any disclaimer, the term of this patent is extended or adjusted under 35 U.S.C. 154(b) by 116 days.

(21) Appl. No.: 17/906,451

(22) PCT Filed: Apr. 7, 2021

(86) PCT No.: PCT/IB2021/052877
§ 371 (c)(1),
(2) Date: Sep. 15, 2022

(87) PCT Pub. No.: WO2021/214579
PCT Pub. Date: Oct. 28, 2021

(65) Prior Publication Data
US 2023/0136092 A1    May 4, 2023

Related U.S. Application Data

(60) Provisional application No. 63/015,204, filed on Apr. 24, 2020.

(51) Int. Cl.
*G01N 27/22* (2006.01)
*A01D 41/127* (2006.01)
*G01N 33/00* (2006.01)

(52) U.S. Cl.
CPC ......... *G01N 27/223* (2013.01); *A01D 41/127* (2013.01); *A01D 41/1277* (2013.01); *G01N 27/226* (2013.01); *G01N 33/0098* (2013.01)

(58) Field of Classification Search
CPC ............... G01N 27/223; G01N 27/226; G01N 33/0098; A01D 41/127; A01D 41/1277
(Continued)

(56) References Cited

U.S. PATENT DOCUMENTS

| 3,430,357 A | 3/1969 | Perry |
| 5,101,163 A | 3/1992 | Agar |

(Continued)

FOREIGN PATENT DOCUMENTS

| AU | 2019201061 A1 | 9/2019 |
| DE | 4105857 A1 | 8/1992 |

(Continued)

OTHER PUBLICATIONS

Georg Kormann: Untersuchungen zur Integration kontinuierlich arbeitender Feuchtemesssysteme in ausgewahlte Futtererntemaschinen11, Dissertation, May 18, 2001 (May 18, 2001), XP055654213, pp. 9-18.

(Continued)

*Primary Examiner* — Raul J Rios Russo

(57) ABSTRACT

An agricultural machine has a capacitive sensor that includes a transmitter assembly having a signal driver, at least one guard driver, and at least one sensing circuit configured to detect an output of the signal driver. At least one sensing electrode is powered by the signal driver. At least one guard electrode is powered by the guard driver. The guard electrode is oriented such that a first electric field emanating from the sensing electrode is shaped at least in part by a second electric field emanating from the guard electrode. A method includes broadcasting a first electric field from a sensing electrode into a volume containing crop material, broadcasting a second electric field from a guard electrode, measuring an attribute related to the first electric field, and correlating the measured attribute related to the (Continued)

first electric field to a property of the crop material in the volume.

23 Claims, 10 Drawing Sheets

(58) Field of Classification Search
USPC .......................................................... 324/664
See application file for complete search history.

(56) References Cited

U.S. PATENT DOCUMENTS

| | | |
|---|---|---|
| 5,560,246 A | 10/1996 | Bottinger et al. |
| 5,572,160 A | 11/1996 | Wadell |
| 5,708,369 A | 1/1998 | Horn |
| 5,835,054 A | 11/1998 | Warhus |
| 5,930,988 A | 8/1999 | Hanson |
| 6,121,782 A | 9/2000 | Adams |
| 6,215,293 B1 | 4/2001 | Yim |
| 6,512,475 B1 | 1/2003 | Bogatyrev et al. |
| 6,806,821 B2 | 10/2004 | McLemore |
| 7,068,050 B2 | 6/2006 | Steele et al. |
| 7,298,312 B2 | 11/2007 | McLemore |
| 7,307,575 B2 | 12/2007 | Zemany |
| 7,448,880 B2 | 11/2008 | Osaka |
| 10,290,948 B2 | 5/2019 | Hoffman et al. |
| 10,371,558 B2 | 8/2019 | Tevs et al. |
| 10,408,645 B2 | 9/2019 | Blank et al. |
| 10,448,570 B2 | 10/2019 | Graeve et al. |
| 2003/0146767 A1 | 8/2003 | Steele et al. |
| 2004/0077943 A1 | 4/2004 | Meaney et al. |
| 2004/0100285 A1 | 5/2004 | Rains |
| 2004/0190377 A1 | 9/2004 | Lewandowski et al. |
| 2006/0176062 A1 | 8/2006 | Yang et al. |
| 2009/0033343 A1* | 2/2009 | Reynolds ............ H03K 17/9622 324/688 |
| 2011/0193574 A1* | 8/2011 | De Boer .............. G01D 5/2417 324/688 |
| 2013/0088245 A1 | 4/2013 | Sezginer |
| 2015/0285752 A1* | 10/2015 | Kozicki ................. B65G 43/00 324/649 |
| 2018/0325028 A1 | 11/2018 | Rotole et al. |
| 2018/0325029 A1 | 11/2018 | Rotole et al. |
| 2018/0325031 A1 | 11/2018 | Rotole et al. |
| 2019/0021229 A1 | 1/2019 | Treffer et al. |
| 2019/0110394 A1 | 4/2019 | VanNahmen |
| 2020/0333278 A1* | 10/2020 | Locken ................. G01N 27/226 |
| 2021/0356298 A1* | 11/2021 | Althaus ................ B60R 16/027 |
| 2023/0358707 A1* | 11/2023 | Honeyman ........ A01D 41/1271 |

FOREIGN PATENT DOCUMENTS

| | | |
|---|---|---|
| EP | 0 843 959 A1 | 5/1998 |
| EP | 2927675 A1 | 10/2015 |
| GB | 2196129 A | 4/1988 |
| GB | 2295897 A | 6/1996 |
| JP | H09145432 A | 6/1997 |
| WO | 2021/214572 A1 | 10/2021 |
| WO | 2021214580 A1 | 10/2021 |

OTHER PUBLICATIONS

UK Intellectual Property Office, Search report for related UK Application No. GB2006617.I, dated Sep. 25, 2020; 5 pages.
European Patent Office, International Search Report related to International Patent Application No. PCT/IB2021/052877, mail date Jul. 5, 2021; 13 pages.
Nurzharina Binti Abd. Karim & Idris Bin Ismail, Soil Moisture Detection Using Electrical Capacitance Tomography (ECT) Sensor, May 2011; 6 pages.

* cited by examiner

AGRICULTURAL MACHINES COMPRISING CAPACITIVE SENSORS, AND RELATED METHODS AND APPARATUS

CROSS-REFERENCE TO RELATED APPLICATION APPLICATIONS

This application is a national phase entry under 35 U.S.C. § 371 of International Patent Application PCT/IB2021/052877, filed Apr. 7, 2021, designating the United States of America and published in English as International Patent Publication WO 2020/214579 A1 on Oct. 28, 2021, which claims the benefit of the filing date of U.S. Provisional Patent Application 63/015,204, "Agricultural Machines Comprising Capacitive Sensors, and Related Methods and Apparatus," filed Apr. 24, 2020, the entire disclosure of which is incorporated herein by reference.

FIELD

Embodiments of the present disclosure relate generally to sensors and methods of measuring material properties, such as of harvested crops. In particular, embodiments relate to methods and apparatus for generating electric fields that interact with materials.

BACKGROUND

When harvesting crops, information about the properties of the crop material (e.g., mass flow, moisture content, crop density, etc.) can be used to make decisions about how and when to operate machinery for improved yield. To increase the speed and efficiency of machines, it would be beneficial to have sensors that can quickly detect properties of crop material without interfering with operation of the machines.

Such sensors could also be used in other situations in which a nondestructive test (and potentially a non-contact test) is desirable, such as in detecting material in packages, in buildings (e.g., within wall structures), in manufacturing processes, mining, etc.

BRIEF SUMMARY

In some embodiments, an agricultural machine has a capacitive sensor that includes a transmitter assembly having a signal driver, at least one guard driver, and at least one sensing circuit configured to detect an output of the signal driver. At least one sensing electrode is powered by the signal driver. At least one guard electrode is powered by the at least one guard driver. The at least one guard electrode is oriented such that a first electric field emanating from the at least one sensing electrode is shaped at least in part by a second electric field emanating from the at least one guard electrode.

A method includes broadcasting a first electric field from a sensing electrode into a volume containing crop material, broadcasting a second electric field from at least one guard electrode adjacent the sensing electrode, measuring an attribute related to the first electric field, and correlating the measured attribute related to the first electric field to a property of the crop material in the volume. At least some field lines of the first electric field emanate from the sensing electrode through the volume. The presence of the second electric field changes a shape of the field lines of the first electric field.

BRIEF DESCRIPTION OF THE DRAWINGS

While the specification concludes with claims particularly pointing out and distinctly claiming what are regarded as embodiments of the present disclosure, various features and advantages of embodiments of the disclosure may be more readily ascertained from the following description of example embodiments when read in conjunction with the accompanying drawings, in which:

DETAILED DESCRIPTION

Figure 1:
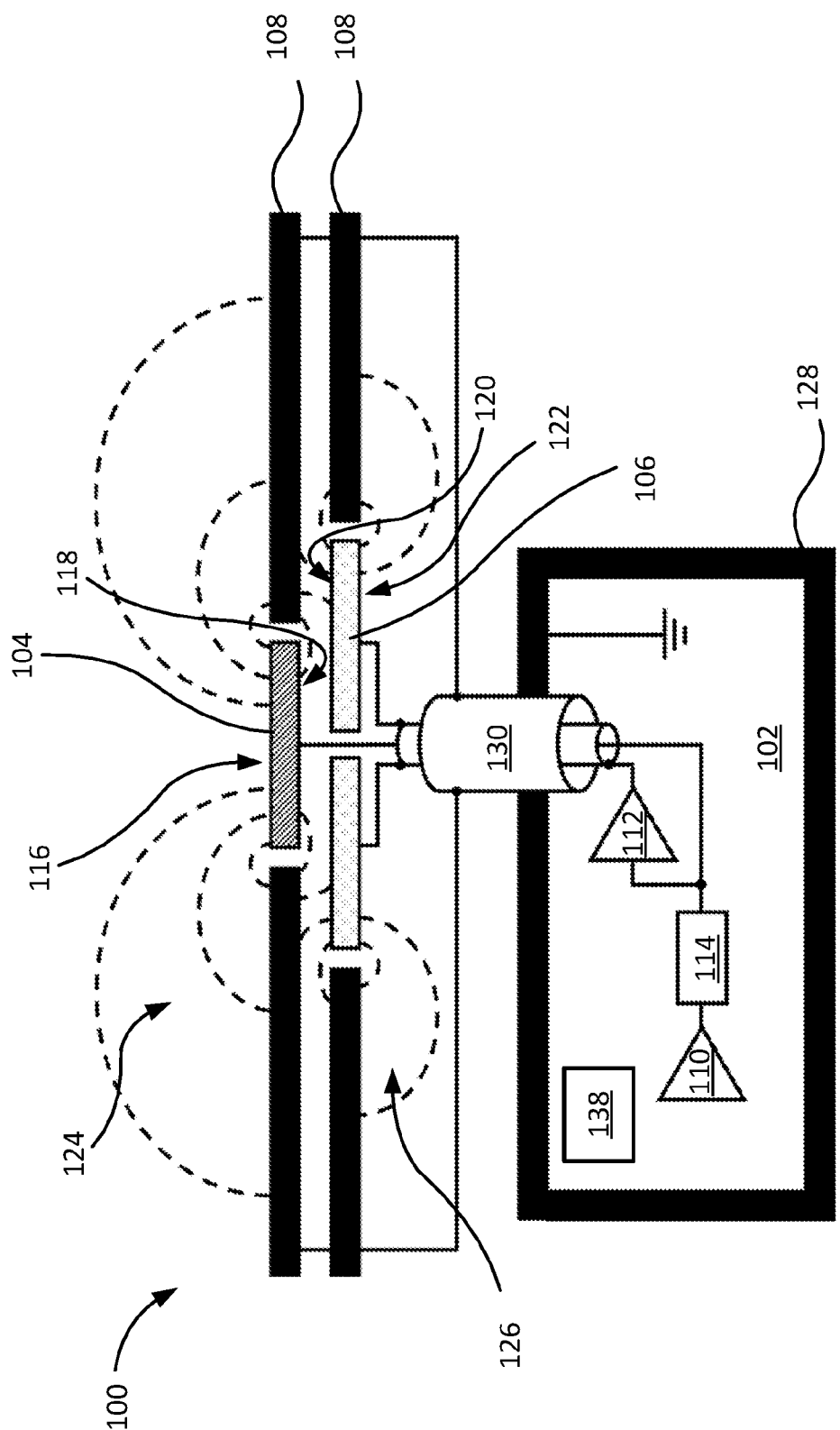
FIG. 1 is a simplified schematic view illustrating a capacitive sensor.

The illustrations presented herein are not actual views of any machine, sensor, or portion thereof, but are merely idealized representations that are employed to describe example embodiments of the present disclosure. Additionally, elements common between figures may retain the same numerical designation.

The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, the description provided below does not include all elements to form a complete structure or assembly. Only those process acts and structures necessary to understand the embodiments of the disclosure are described in detail below. Additional conventional acts and structures may be used. The drawings accompanying the application are for illustrative purposes only, and are thus not drawn to scale.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other, compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter).

FIG. 1 is a simplified diagram illustrating a capacitive sensor 100. The sensor 100 includes a transmitter assembly 102, at least one sensing electrode 104, and at least one guard electrode 106. The sensor 100 may also include one or more ground electrode(s) 108. The sensor 100 may be considered a "guarded" capacitive sensor because it can generate two electric fields 124, 126, which can interact with one another and shape one another (i.e., one can "guard" the other). In particular, the field 124 associated with the sensing electrode(s) 104 may be considered the sensing field, and the field 126 associated with the guard electrode(s) 106 may be considered the guard field. The guard field 126 may be used to shape the sensing field 124, as described in further detail below.

The transmitter assembly 102 shown in FIG. 1 includes a signal driver 110, a guard driver 112, and a sensing circuit 114. A power source 138 may provide power to the components of the transmitter assembly 102, and may be within or external to the transmitter assembly 102. As illustrated, the signal driver 110 may be configured to provide a selected voltage to the sensing electrode 104 (which may be a constant or time-variable voltage). The sensing circuit 114 may measure the output of the signal driver 110, such as the current or power levels required to provide the selected voltage. The guard driver 112 may be configured to provide a selected voltage to the guard electrode 106, and may optionally receive its power from the power source 138 via the signal driver 110. In other embodiments, the guard driver 112 receives its power directly from the power source 138.

The sensing electrode 104 may have a major front surface 116 and a major rear surface 118 on an opposite side of the sensing electrode 104, each of which may be generally planar. In other embodiments, the major front surface 116 and the major rear surface 118 may be curved or of another shape. For example, if the sensor 100 is designed to measure material in a tube, the major front surface 116 and the major rear surface 118 may have curvature matching the curvature of the tube. The major rear surface 118 may be generally aligned with the major front surface 116. For example, if both are generally planar, the major front surface 116 may be parallel to the major rear surface 118 and separated by a distance smaller than either dimension (e.g., length or width) of the major front surface 116. The sensing electrode 104 is powered by the signal driver 110 of the transmitter assembly 102.

The guard electrode 106 may have similar geometry, with a major front surface 120 and a major rear surface 122. The guard electrode 106 is powered by the guard driver 112 of the transmitter assembly 102. The major front surface 120 of the guard electrode 106 may be located adjacent the major rear surface 118 of the sensing electrode 104, such as separated by a distance smaller than the shortest of the lateral length or width of the sensing electrode 104.

FIG. 1 depicts a few field lines of the electric field 124 of the sensing electrode 104 and the electric field 126 of the guard electrode 106. The major front surface 120 of the guard electrode 106 may be oriented such that the field 124 of the sensing electrode 104 is shaped at least in part by the field 126 of the guard electrode 106. As shown in FIG. 1, the electrodes may be positioned such that the distance from the major rear surface 118 of the sensing electrode 104 to the major front surface 120 of the guard electrode 106 is smaller than the distance from the major rear surface 118 of the sensing electrode 104 to the ground electrode 108 (or to any other electrode, if any, or any other object). The shortest path from any point on the major rear surface 118 of the sensing electrode 104 outward (i.e., in a direction generally downward in the view of FIG. 1) may intersect the major front surface 120 of the guard electrode 106 before reaching any other object. In this way, the guard electrode 106 may prevent other objects from interfering with the portion of the field 124 emanating from the major rear surface 118 of the sensing electrode 104. Thus, the guard electrode 106 may "guard" the major rear surface 118 of the sensing electrode 104 from interacting with other electrodes, and may cause the sensing electrode 104 to function similar to a theoretical one-sided electrode (i.e., with no field lines emanating from the major rear surface 118 of the sensing electrode 104 past the guard electrode 106). In such an arrangement, the field lines of the field 124 emanating from the major rear surface 118 of the sensing electrode 104 are spaced more densely than field lines emanating from the major front surface 116. Thus, the field lines of the field 124 of the sensing electrode 104 do not pass or intersect the guard electrode 106.

The ground electrode 108, if present, may be separated from and coplanar with the sensing electrode 104. In such embodiments, some field lines of the field 124 of the sensing electrode 104 may have an arcuate shape extending outward from the major front surface 116 of the sensing electrode 104 to the ground electrode 108. Some field lines of the field 126 of the guard electrode 106 may have an arcuate shape extending outward from the major rear surface 122 of the guard electrode 106 to the ground electrode 108 (which may be the same ground electrode 108 or a different ground electrode 108). The ground electrode(s) 108 may laterally surround the sensing electrode 104 and/or the guard electrode 106. In some embodiments, the ground electrode 108 may include a shield 128 protecting the transmitter assembly 102, such that the fields 124, 126 do not interfere with the operation of the transmitter assembly 102. Field lines emanating from the sensing electrode 104 and the guard electrode 106 may intersect the ground electrode 108.

In some embodiments, a cable 130 may connect the transmitter assembly 102 to the electrodes 104, 106, 108. The cable 130 may be a coaxial cable having two or more conductors sharing a common axis. For example, the cable 130 may have a first conductor, shown as an inner core conductor (e.g., a wire) of a triaxial cable, connecting the sensing circuit 114 to the sensing electrode 104. The cable 130 may have a second conductor, shown as an intermediate cylindrical conductor of a triaxial cable, connecting the guard driver 112 to the guard electrode 106. The cable 130 may have a third conductor, shown as an outer cylindrical conductor of a triaxial cable, connecting the ground electrode 108 to a physical ground. In some embodiments, the ground electrode 108 may be omitted, and thus, the cable 130 may be a biaxial cable, having only two conductors.

The transmitter assembly 102 is configured to provide a first signal to the sensing electrode 104 and a second signal to the guard electrode 106. For example, and as discussed above, the transmitter assembly 102 may send preselected voltage signals to the electrodes 104, 106. In some embodiments, the voltage provided to each electrode 104, 106 may be identical in magnitude but electrically isolated. Isolated outputs may enable the transmitter assembly 102 to distinguish material sensed in the volume encompassed by field 124 from 126, and that the interference between them may be insignificant. That is, the magnitude of the difference between the two fields 124, 126 as they extend outward, and/or the field established between the major rear surface 118 of the sensing electrode 104 and the major front surface 120 of the guard electrode 106 may be significantly smaller (e.g., at least one order of magnitude, at least two orders of magnitude, etc.) than the magnitude of the fields 124, 126 themselves.

The transmitter assembly 102 may provide the selected signals to the electrodes 104, 106 using the signal driver 110 and the guard driver 112. The power source 138 may provide power to the signal driver 110 and the guard driver 112.

In some embodiments, the transmitter assembly 102 may be configured to provide a first voltage to the sensing electrode 104 and a second, different voltage to the guard electrode 106. The second voltage may be offset from the first voltage by a preselected amount. These different voltages may be useful for active sensing of material, using changing field parameters (e.g., detection area size or shape, direction of view, calibration, etc.).

The sensing circuit 114 may measure the output of the signal driver 110, such as the current or power levels required to provide the selected voltage. The guard driver 112 may be configured to provide a selected voltage to the guard electrode 106, and may optionally receive its power from the power source 138 via the signal driver 110. Though the transmitter assembly 102 is described as providing a known voltage and measuring known power or current, other attributes of the field may be measured, such as current, power, voltage, reactance, impedance, resonance, capacitance, frequency, permittivity, time, etc.

The sensing field 124 may have a response curve, meaning that its attributes vary in a particular way in response to different conditions. For example, the sensing field 124 may have a field strength that decreases in proportion to $1/r^2$ or $1/r^3$, where r is the distance from the major front surface 116 of the sensing electrode 104. If the field 124 is formed by electromagnetic radiation having a frequency that excites water molecules, moisture in the field 124 can affect the field lines of the field 124. The material in the field 124 may cause a change in the electrical load provided by the signal driver 110 to generate the field 124, and may be measured by the sensing circuit 114. The use of electromagnetic sensors for characterizing crop material is described in more detail in U.S. Provisional Patent Application 63/015,219, "Methods of Measuring Crop Material," filed on the same date as this application in the name of Honeyman, et al.

Figure 2:
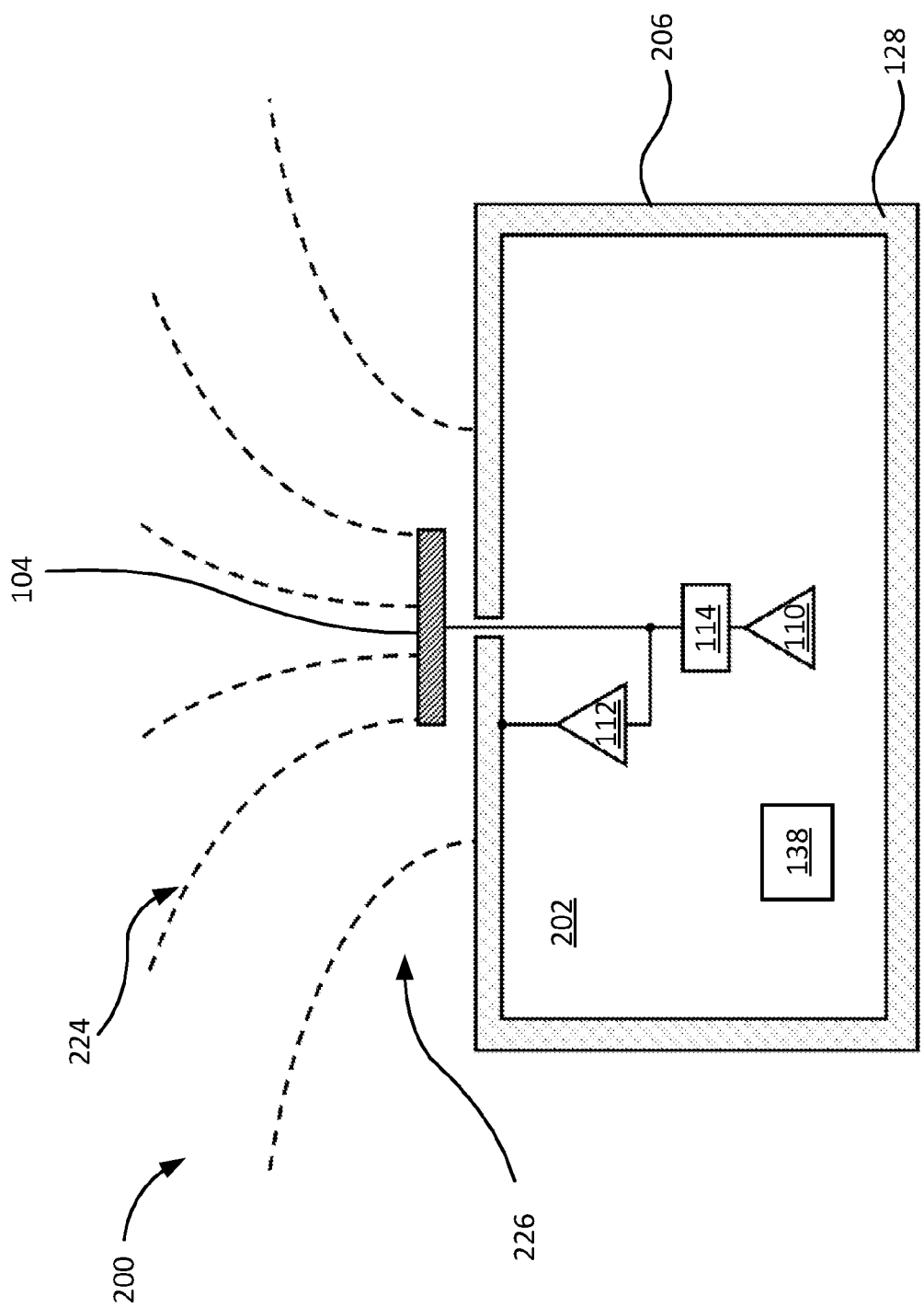
FIG. 2 is a simplified schematic view illustrating another capacitive sensor.

FIG. 2 is a simplified diagram illustrating another capacitive sensor 200. The sensor 200 includes a transmitter assembly 202, at least one sensing electrode 104, and at least one guard electrode 206. The sensor 200 is depicted as lacking a ground electrode, and with the guard electrode 206 also serving as the shield 128 to protect the transmitter assembly 202 from interference by the fields 224, 226 emanating from the electrodes 104, 206. As depicted, the fields 224, 226 may extend generally outward to another physical ground. The electrodes 104, 206 may be arranged such that the guard field 226 shapes the sensing field 224. In the embodiment shown, the field lines of the sensing field 224 extend generally upward and outward.

Figure 3:
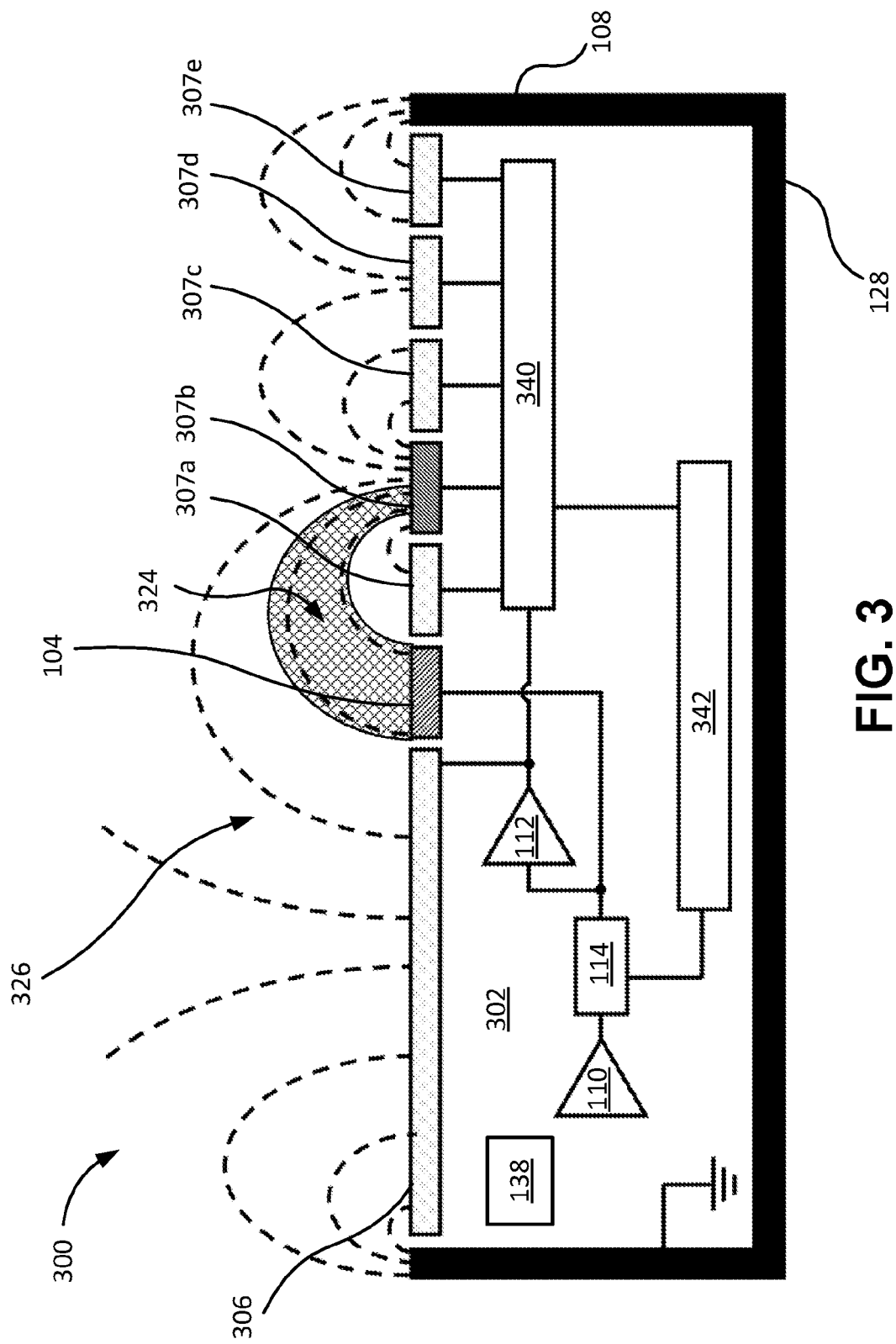
FIG. 3 is a simplified schematic view illustrating yet another a capacitive sensor.

FIG. 3 is a simplified diagram illustrating another capacitive sensor 300. The sensor 300 includes a transmitter assembly 302, a sensing electrode 104, a guard electrode 306, switchable electrodes 307a-307e, and a ground electrode 108 (which may operate as a shield 128 to protect the transmitter assembly 302 from interference, either alone or in combination with the guard electrode 306). The major front surfaces of the electrodes 104, 306, 307a-307e may be generally coplanar. In embodiments in which the major front surfaces are curved or another shape, the curvature of the major front surfaces of the electrodes 104, 306, 307a-307e may be generally continuous.

The transmitter assembly 302 may include a signal driver 110, a guard driver 112, a sensing circuit 114, and a power source 138, as discussed above. Furthermore, the transmitter assembly 302 may include a multiplexor 340 and a controller 342. The multiplexor 340 may be configured to selectively provide power from the guard driver 112 to individual switchable electrodes 307a-307e. The controller 342 can drive the multiplexor 340 to change which of the switchable electrodes 307a-307e are powered and which are grounded. Thus, the switchable electrodes 307a-307e may, when so powered, operate as guard electrodes, similar to the guard electrode 306. The multiplexor 340 may also ground one of the switchable electrodes 307a-307e. As depicted in FIG. 3, the electrode 307b is grounded by the multiplexor 340, while the electrodes 307a, 307c, 307d, and 307e are powered by the guard driver 112. Thus, field lines of the guard field 326 connect the guard electrodes 306, 307a, 307c, 307d, and 307e to the grounded switchable electrode 307b and/or to the ground electrode 108. The field lines of the sensing field 324 connect the sensing electrode 104 to the grounded switchable electrode 307b. The approximate shape of the sensing field 324 is shaded in FIG. 3.

Figure 4:
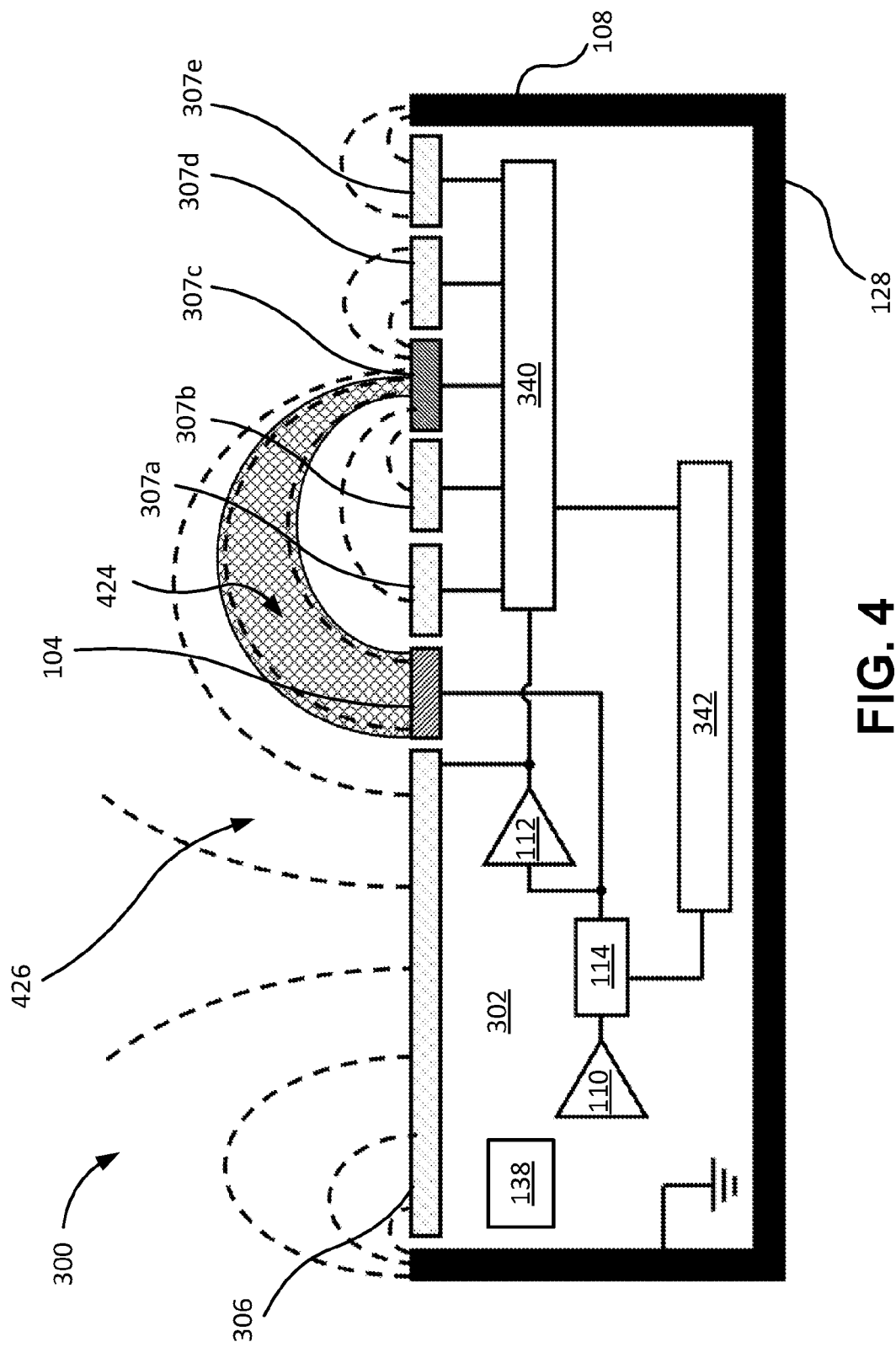
FIG. 4 is another view of the sensor of FIG. 3.

FIG. 4 is a simplified diagram illustrating how the shape of the fields changes when the multiplexor 340 changes which electrodes are powered. In particular, switchable electrode 307c is depicted as grounded in FIG. 4, and the guard field 426 has field lines connecting the electrodes 306, 307a, 307b, 307d, and 307e to the grounded switchable electrode 307c and/or to the ground electrode 108. The field lines of the sensing field 424 connect the sensing electrode 104 to the grounded switchable electrode 307c. The approximate shape of the sensing field 424 is shaded in FIG. 4. By changing which of the switchable electrodes 307a-307e are powered and which are grounded, the shape of the sensing field 324, 424 can be changed without changing the physical location of the electrodes 104, 108, 306, 307a-307e. The multiplexor 340 may likewise ground any of the switchable electrodes 307a-307e to cause different sensing fields. Thus, the multiplexor 340 may enable rapid switching between sensing fields of different size and/or shape without physical movement of the sensor 300 or components thereof.

Figure 5:
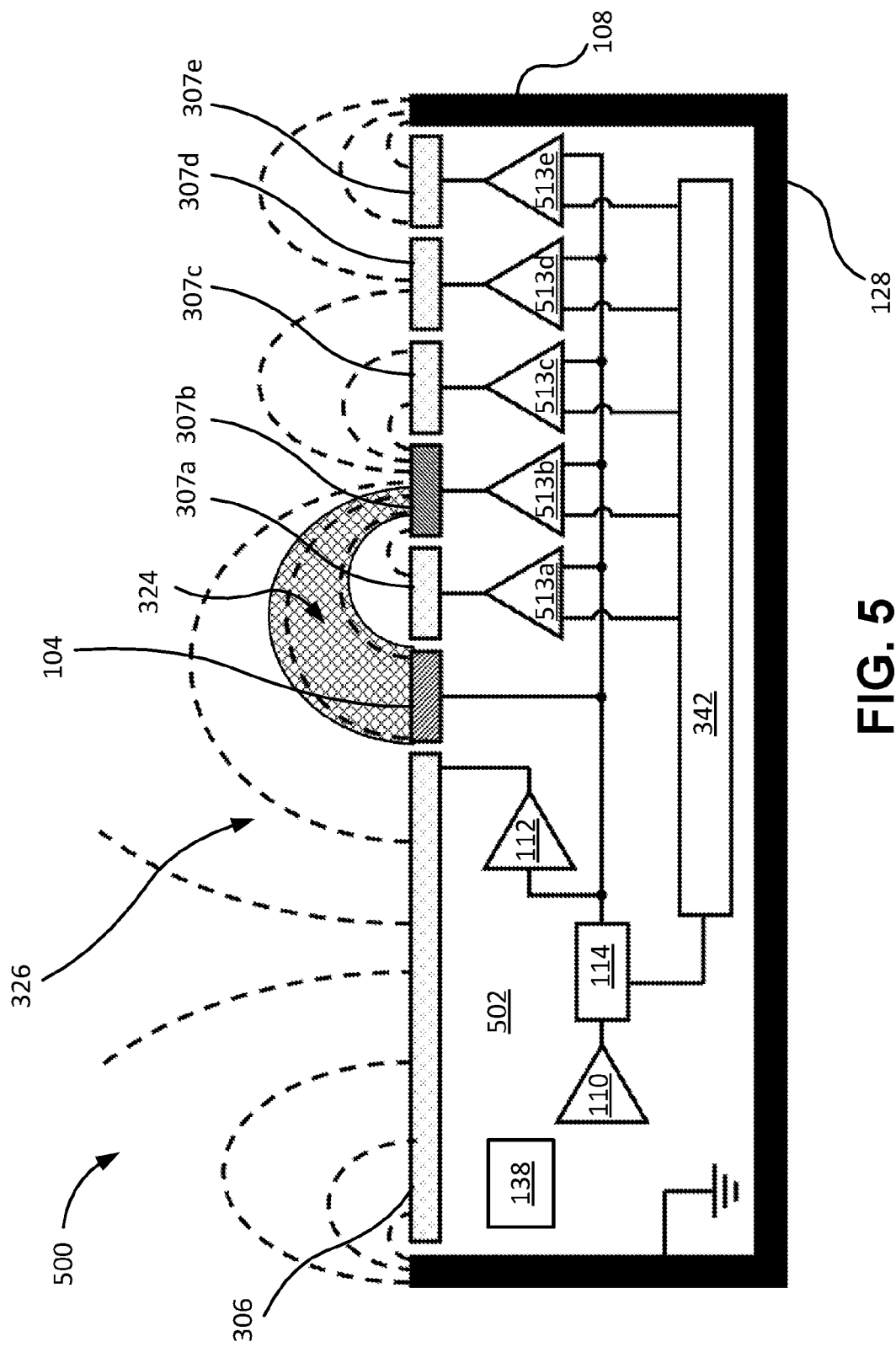
FIG. 5 is a simplified schematic view illustrating another capacitive sensor.

FIG. 5 is a simplified diagram illustrating another capacitive sensor 500. The sensor 500 may be generally configured similar to the sensor 300 shown in FIGS. 3 and 4, including a transmitter assembly 502, a sensing electrode 104, a guard electrode 306, switchable electrodes 307a-307e, and a ground electrode 108 (which also operates as a shield 128 to protect the transmitter assembly 302 from interference). The transmitter assembly 502 differs from the transmitter assembly 302 shown in FIG. 3 in that it includes switched guard drivers 513a-513e, instead of the multiplexor 340. One switched guard driver 513a-513e is configured to power each of the switchable electrodes 307a-307e. The switched guard drivers 513a-513e may be independently driven by the controller 342, such that the transmitter assembly 502 can generate different sensing and guard fields in a similar manner as the sensor 300.

Figure 6:
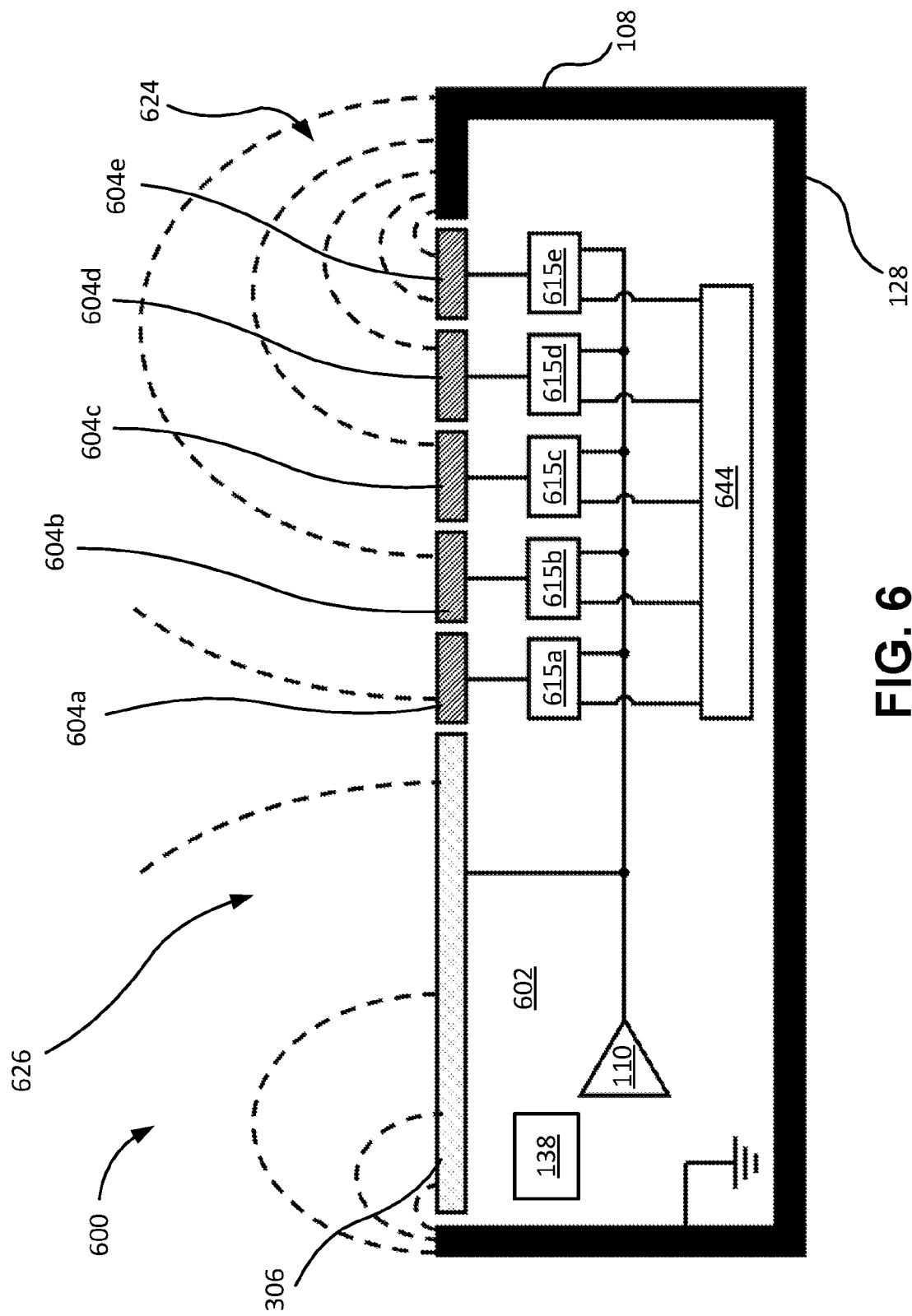
FIG. 6 is a simplified schematic view illustrating another capacitive sensor.

In some embodiments, different sensing electrodes may form different sensing fields concurrently. For example, FIG. 6 is a simplified diagram illustrating another capacitive sensor 600. The sensor 600 includes a transmitter assembly 602, sensing electrodes 604a-604e, a guard electrode 306, and a ground electrode 108 (which also operates as a shield 128 to protect the transmitter assembly 602 from interference).

The transmitter assembly 602 includes a signal driver 110 configured to provide selected voltage(s) to the guard electrode 306 and the sensing electrodes 604a-604e. Sensing circuits 615a-615e may selectivity detect the output of the signal driver 110 to each corresponding sensing electrode 604a-604e. An output driver 644 may control voltages applied to each of the sensing electrodes 604a-604e. Sensing fields 624 may form between each sensing electrode 604a-604e and the ground electrode 108. Each sensing electrode 604a-604e may generate a separate sensing field, and the size and shape of each is dependent on the distance from each sensing electrode 604a-604e to the ground electrode 108, the position of the other sensing electrodes 604a-604e, the power levels of each sensing electrode 604a-604e, the size and shape of each sensing electrode 604a-604e, etc. The different sensing fields 624 may shape one another, and may together be used to measure properties of material in different volumes or in different ways.

Each of the sensors 300, 500, 600 shown in FIGS. 3 through 6 include a guard electrode 306 depicted on the left of the sensing electrode(s) 104 or 604a-604e. However, in some embodiments, the guard electrode 306 may be omitted and replaced by additional switchable electrodes or sensing electrodes. In such embodiments, the additional switchable electrodes or sensing electrodes may serve to shape the sensing fields and/or limit the influence of external electric fields on the sensing fields. Furthermore, the sensors 100, 200, 300, 500, 600 shown in FIG. 1 through 6 are depicted as unitary structures (either combined with or separate from the transmitter assemblies), but the various electrodes may also be configured to be separately mounted on a body or on separate bodies in such a manner that fields generated affect one another.

The sensors 100, 200, 300, 500, 600 described herein may carried by an agricultural vehicle frame and may be used to measure crop material in crop-harvesting operations, such as in combines, windrowers, balers, etc. The sensors 100, 200, 300, 500, 600 and methods herein may also be used to measure properties of any other type of material, and may be used in various industries, such as mining, chemical processing, food processing and packaging, shipping, security (e.g., nondestructively detecting properties of unopened parcels), construction (e.g., detecting materials inside walls), manufacturing (e.g., nondestructive parts inspection), etc.

Figure 7:
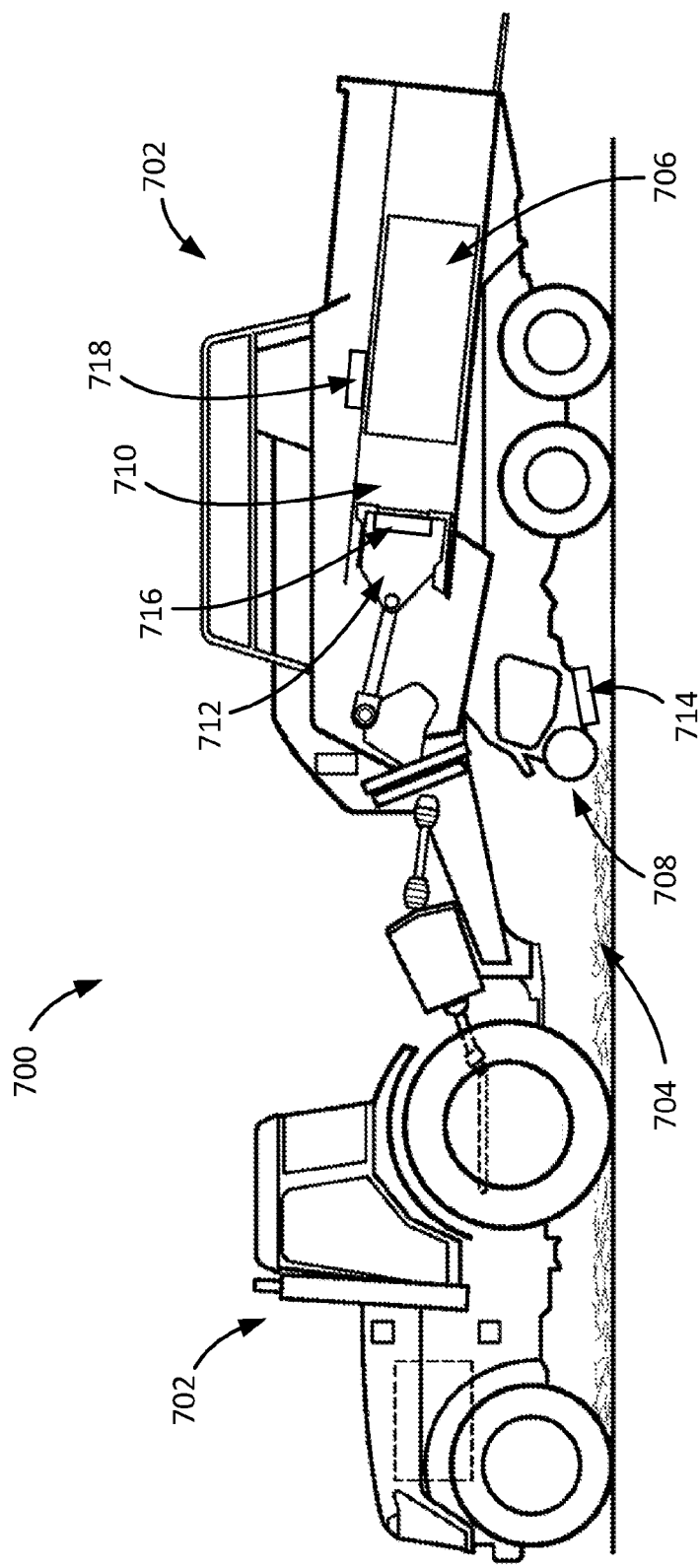
FIG. 7 is a simplified side view of a baling system, which may include the sensors shown in FIGS. 1 through 6.

FIG. 7 is a simplified side view of a baling system 700 including a tractor 702 towing a baler 704, each of which include vehicle frames. The baling system 700 is operable to receive loose crop material 704, form it into individual charges, and compress the charges to form a bale 706. The baler 702 may include a stuffing component 708, a forming chamber 710, and a plunger 712. The stuffing component 708 picks up the loose crop material 704, and transfers it to the forming chamber 710. The plunger 712 compresses the loose crop material 704 to form the bale 706 or a portion thereof. Baling systems are described in more detail in International Patent Application Publication WO 2019/123039, "Baler with NIR Sensor in Plunger Face," published 27 Jun. 2019. As depicted in FIG. 7, the baler 704 may include one or more sensors 714, 716, 718. For example, the sensor 714 is depicted adjacent to the stuffing component 708 to detect properties of the loose crop material 704 entering the baler 704. The sensor 716 is depicted on or in the plunger 712 to detect properties of the crop material before or during compression. The sensor 718 is depicted adjacent the bale 706 to detect properties of the crop material in the bale 706 as the bale 706 is ejected from the baler 704. The sensors 714, 716, 718 may be a sensor 100, 200, 300, 500, 600 as shown in FIGS. 1 through 6 and described above. Additional sensors may be in other locations within the baling system 700, such as carried by the tractor 702. Multiple sensors may be used to characterize whether operating parameters of the baling system 700 are effective, and may enable a control system to adjust the operating parameters (e.g., ground speed, compaction force, etc.) to improve the properties of the bale 706. For example, the sensor(s) 714, 716, 718 may be used to measure the moisture content and/or density of crop material in the bales 706.

Figure 8:
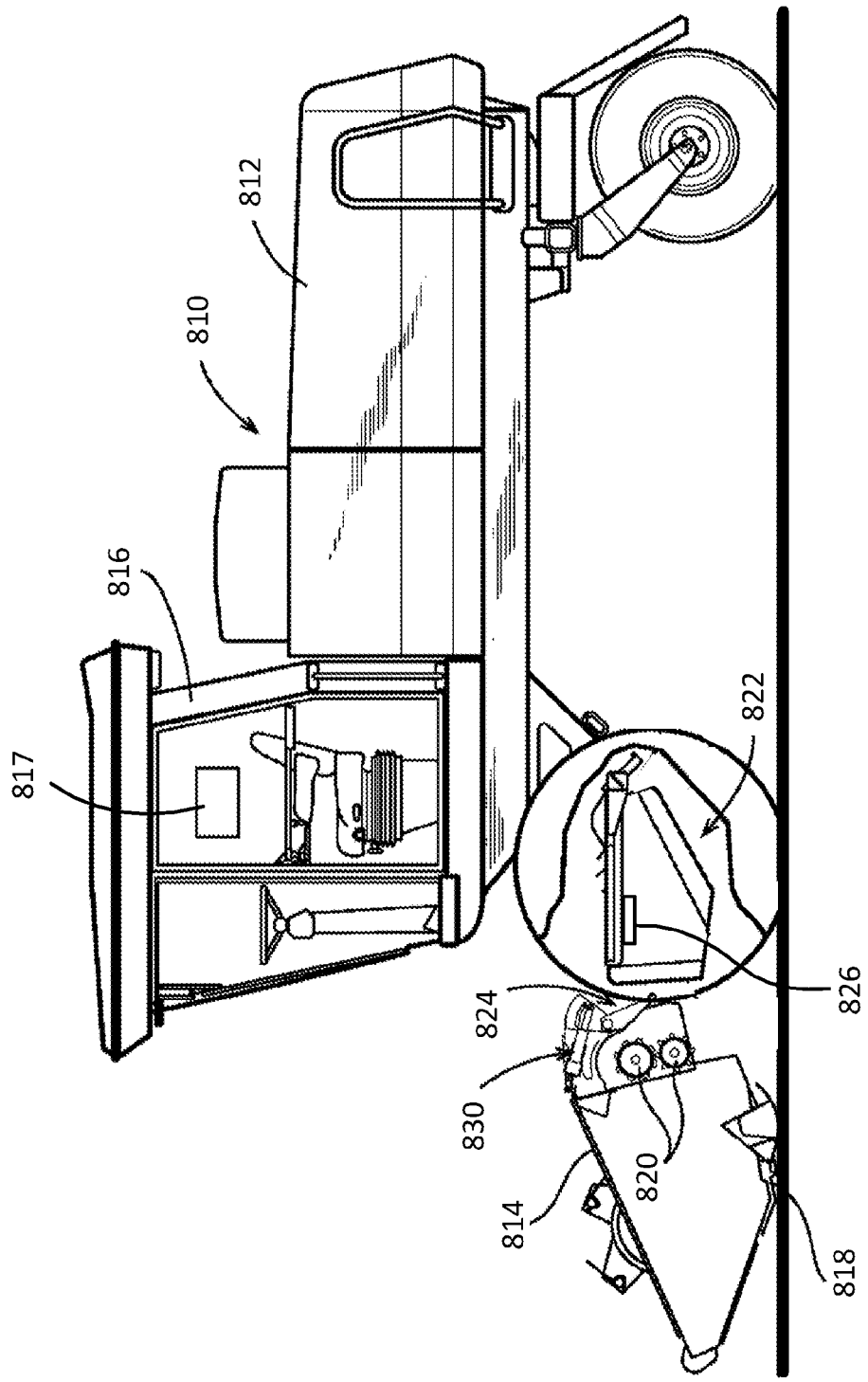
FIG. 8 is a simplified side view of a windrower, which may include the sensors shown in FIGS. 1 through 6.

FIG. 8 is a simplified side view of a self-propelled windrower 810. In some embodiments, pull-type or other types of harvesting machines may be used. The windrower 810 broadly includes a self-propelled tractor 812 having a vehicle frame and a harvesting header 814 attached to and carried by the front of the tractor 812. An operator drives the windrower 810 from a cab 816, which includes an operator station having a tractor seat and one or more user interfaces (e.g., FNR joystick, display monitor, switches, buttons, etc.) that enable the operator to control various functions of the tractor 812 and header 814. In one embodiment, a controller 817 or computing system is disposed in the cab 816, though in some embodiments, the controller 817 may be located elsewhere or include a distributed architecture having plural computing devices, coupled to one another in a network, throughout various locations within the tractor 812 (or in some embodiments, located in part externally and in remote communication with one or more local computing devices).

The header 814 includes a cutter 818, a conditioning system, a swathboard 824, and a forming shield assembly 822. The cutter 818 is configured for severing standing crops as the windrower 810 moves through the field. The conditioning system, in the depicted embodiment, includes one or more pairs of conditioner rolls 820. The forming shield assembly 822 may include a pair of rearwardly converging windrow forming shields located behind the conditioner rolls 820. The swathboard 824 is located between the conditioner rolls 820 and the forming shield assembly 822. In some embodiments, the conditioning system may be of a different design, such as a flail-type conditioning system. The swathboard 824 and/or the forming shield assembly 822 may be adjusted by one or more actuators 830.

A sensor 826, which may be any of the sensors 100, 200, 300, 500, 600 described above and shown in FIGS. 1 through 6, may be carried by the windrower 810 or the header 814 such that it can measure the crop material being cut by the header 814 and formed into a windrow. The measuring device 826 may communicate with the controller 817 such that the controller 817 can change operating parameters of the windrower 810 and/or the header 814 (e.g., a position of one or more of the actuators 830). In some embodiments, the measuring device 826 may report information to the operator, and the operator may make changes to the operating parameters of the windrower 810 and/or the header 814. Changing operating parameters of a windrower 810 or header 814 based on information about the crop is described in more detail in U.S. Provisional Patent Application 63/015,183, "Agricultural Machines and Methods for Controlling Windrow Properties," filed on the same date as this application in the name of Hamilton, et al.

Figure 9:
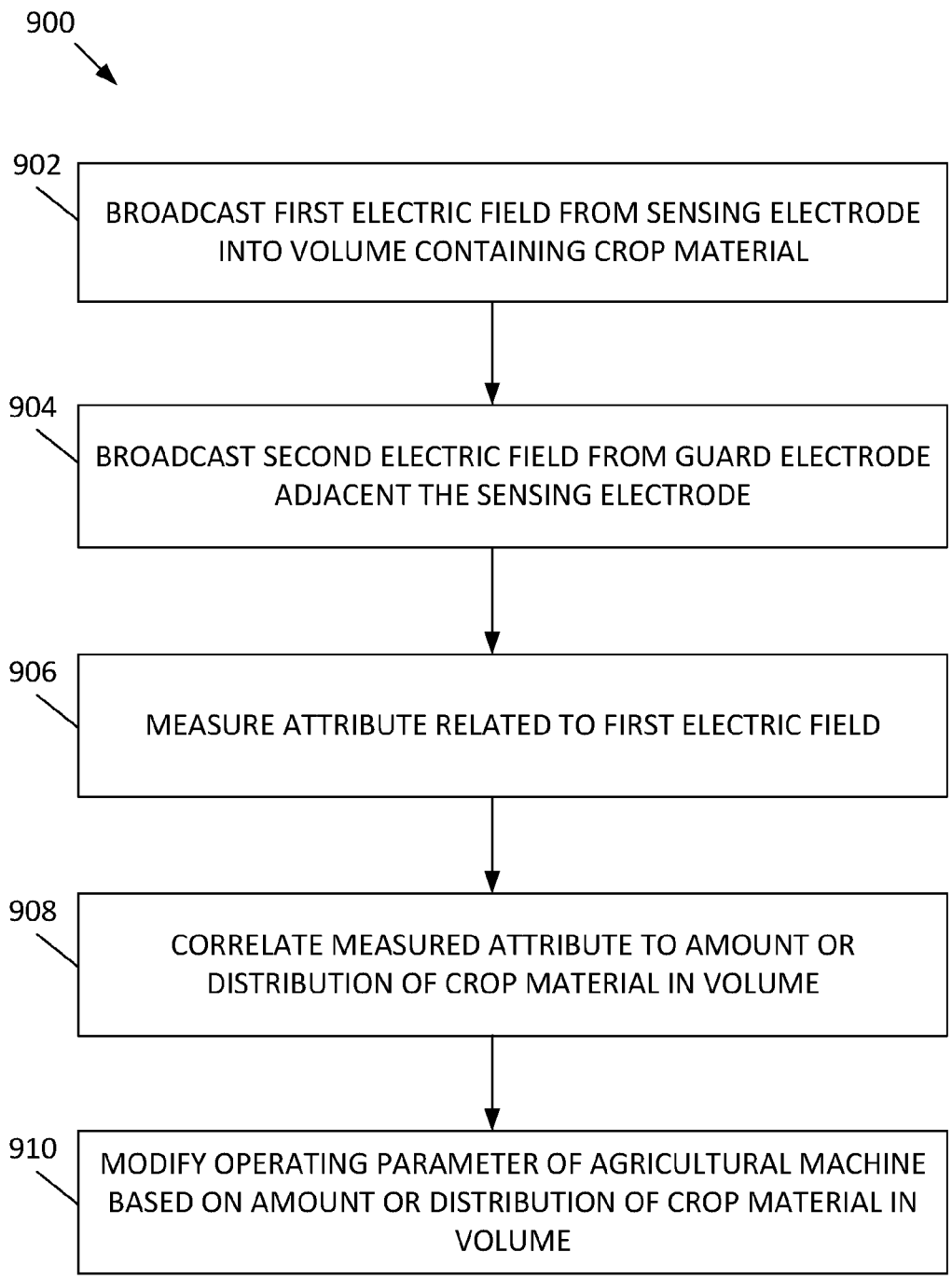
FIG. 9 is a simplified flow chart illustrating a method of measuring electric fields associated with crop material.

FIG. 9 is a simplified flow chart illustrating a method 900 of measuring electric fields associated with crop material. In block 902, a first electric field is broadcast from a sensing electrode into a volume containing crop material. At least some field lines of the first electric field emanate from the sensing electrode through the volume. The first electric field may be broadcast by applying a first voltage to the sensing electrode, which may be a constant voltage or a variable voltage. In block 904, a second electric field is broadcast from at least one guard electrode adjacent the sensing electrode. The presence of the second electric field changes a shape of the field lines of the first electric field. The second electric field may be broadcast by applying a second voltage to the sensing electrode, which may be the same as or different from the first voltage. In some embodiments, the sensing electrode may be electrically isolated from the guard electrode.

In block 906, an attribute of the first electric field is measured. For example, the attribute measured may be current, power, voltage, reactance, impedance, resonance, capacitance, frequency, permittivity, time, etc. In block 908, the measured attribute is correlated to the first electric field to a property of the crop material in the volume.

In block 910, an operating parameter of an agricultural machine is modified based on the property of crop material in the volume.

Figure 10:
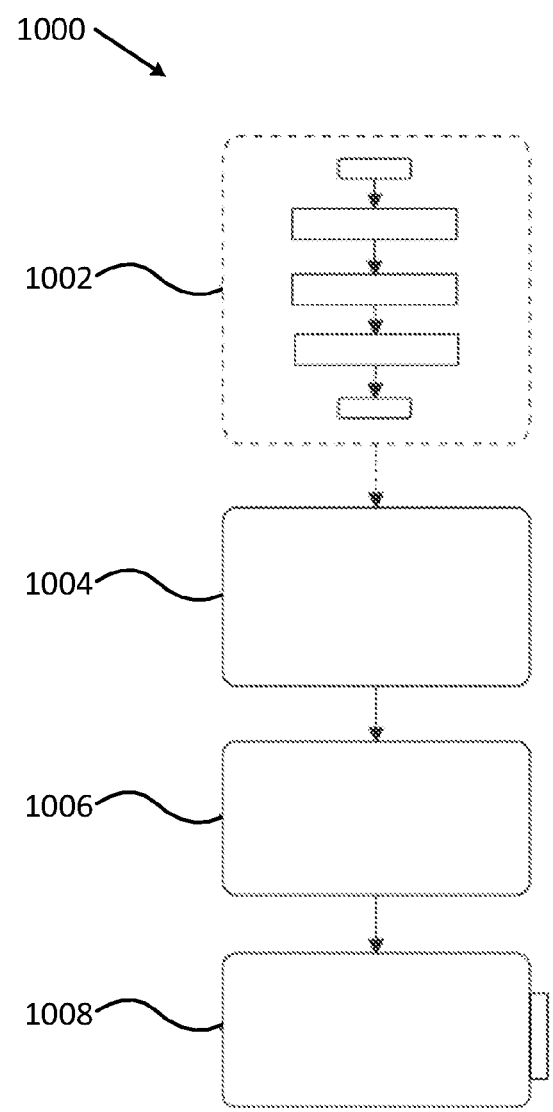
FIG. 10 illustrates an example computer-readable storage medium comprising processor-executable instructions configured to embody one or more of the methods of measuring electric fields associated with crop material, such as the method illustrated in FIG. 9.

Still other embodiments involve a computer-readable storage medium (e.g., a non-transitory computer-readable storage medium) having processor-executable instructions configured to implement one or more of the techniques presented herein. An example computer-readable medium that may be devised is illustrated in FIG. 10, wherein an implementation 1000 includes a computer-readable storage medium 1002 (e.g., a flash drive, CD-R, DVD-R, application-specific integrated circuit (ASIC), field-programmable gate array (FPGA), a platter of a hard disk drive, etc.), on which is computer-readable data 1004. This computer-readable data 1004 in turn includes a set of processor-executable instructions 1006 configured to operate according to one or more of the principles set forth herein. In some embodiments, the processor-executable instructions 1006 may be configured to cause a computer associated with an agricultural machine, such as the baling system 700 (FIG. 7) or the windrower 810 (FIG. 8) to perform operations 1008 when executed via a processing unit, such as at least some of the example method 900 depicted in FIG. 9. In other embodiments, the processor-executable instructions 1006 may be configured to implement a system, such as at least some of the example baling system 700 (FIG. 7) or windrower 810 (FIG. 8). Many such computer-readable media may be devised by those of ordinary skill in the art that are configured to operate in accordance with one or more of the techniques presented herein.

Additional non limiting example embodiments of the disclosure are described below.

Embodiment 1: An agricultural machine comprising a vehicle frame and a capacitive sensor carried by the vehicle frame. The capacitive sensor comprises a transmitter assembly comprising a signal driver, at least one guard driver, and at least one sensing circuit configured to detect an output of the signal driver; at least one sensing electrode powered by the signal driver; and at least one guard electrode powered by the at least one guard driver. The at least one guard electrode is oriented such that a first electric field emanating from the at least one sensing electrode is shaped at least in part by a second electric field emanating from at least one the guard electrode.

Embodiment 2: The agricultural machine of Embodiment 1, wherein the sensor further comprises a cable comprising a first conductor connecting the at least one sensing circuit to the at least one sensing electrode and a second conductor connecting the at least one guard driver to the at least one guard electrode.

Embodiment 3: The agricultural machine of Embodiment 2, wherein the cable comprises a coaxial cable.

Embodiment 4: The agricultural machine of Embodiment 3, wherein the first conductor comprises an inner conductor of the coaxial cable and connects the sensing circuit to the at least one sensing electrode, and wherein the second conductor comprises an outer conductor of the coaxial cable and connects the guard driver to the at least one guard electrode.

Embodiment 5: The agricultural machine of Embodiment 1, further comprising at least one ground electrode.

Embodiment 6: The agricultural machine of Embodiment 5, wherein at least a portion of the at least one ground electrode is separated from and coplanar to the at least one sensing electrode.

Embodiment 7: The agricultural machine of Embodiment 5 or Embodiment 6, wherein the at least one ground electrode laterally surrounds the at least one sensing electrode.

Embodiment 8: The agricultural machine of any one of Embodiment 5 through Embodiment 7, wherein the at least one ground electrode shields the transmitter assembly.

Embodiment 9: The agricultural machine of any one of Embodiment 5 through Embodiment 8, wherein the sensor further comprises a cable comprising a first conductor connecting the at least one sensing circuit to the at least one sensing electrode, a second conductor connecting the at least one guard driver to the at least one guard electrode, and a third conductor connecting the at least one ground electrode to a ground of the transmitter assembly.

Embodiment 10: The agricultural machine of Embodiment 9, wherein the cable comprises a triaxial cable.

Embodiment 11: The agricultural machine of any one of Embodiment 5 through Embodiment 10, wherein field lines emanating from the at least one sensing electrode intersect the at least one ground electrode.

Embodiment 12: The agricultural machine of any one of Embodiment 1 through Embodiment 11, wherein field lines emanating from a major rear surface of the at least one sensing electrode are spaced more densely than field lines emanating from a major front surface of the at least one sensing electrode.

Embodiment 13: The agricultural machine of any one of Embodiment 1 through Embodiment 12, wherein the transmitter assembly is configured to provide a first voltage to the at least one sensing electrode and a second voltage to the at least one guard electrode, wherein the first voltage and the second voltage are identical in magnitude but electrically isolated.

Embodiment 14: The agricultural machine of any one of Embodiment 1 through Embodiment 12, wherein the transmitter assembly is configured to provide a first voltage to the at least one sensing electrode and a second voltage to the at least one guard electrode, wherein the second voltage is offset from the first voltage by a preselected amount.

Embodiment 15: The agricultural machine of any one of Embodiment 1 through Embodiment 14, wherein the at least one guard electrode shields the transmitter assembly.

Embodiment 16: The agricultural machine of any one of Embodiment 1 through Embodiment 15, wherein the signal driver and the at least one guard driver share a common power source.

Embodiment 17: The agricultural machine of any one of Embodiment 1 through Embodiment 16, wherein a major rear surface of the at least one sensing electrode is adjacent a major front surface of the at least one guard electrode.

Embodiment 18: The agricultural machine of Embodiment 17, wherein a shortest path from any point on the major rear surface of the at least one sensing electrode outward intersects the major front surface of the at least one guard electrode before reaching any other object.

Embodiment 19: The agricultural machine of any one of Embodiment 1 through Embodiment 16, wherein a major front surface of the at least one sensing electrode is coplanar with a major front surface of the at least one guard electrode.

Embodiment 20: The agricultural machine of any one of Embodiment 1 through Embodiment 19, wherein the at least one guard electrode comprises a plurality of guard electrodes.

Embodiment 21: The agricultural machine of Embodiment 20, wherein the transmitter further comprises a multiplexor configured to selectively provide power from the at least one guard driver to individual guard electrodes of the plurality.

Embodiment 22: The agricultural machine of Embodiment 21, wherein the sensor further comprises a controller configured to drive the multiplexor.

Embodiment 23: The agricultural machine of Embodiment 20, wherein the at least one guard driver comprises a plurality of switched guard drivers, and wherein each switched guard driver of the plurality is configured to selectively provide power to individual guard electrodes of the plurality.

Embodiment 24: The agricultural machine of Embodiment 23, wherein the transmitter assembly further comprises a controller configured to drive the plurality of switched guard drivers.

Embodiment 25: The agricultural machine of any one of Embodiment 1 through Embodiment 24, wherein the at least one sensing electrode comprises a plurality of sensing electrodes.

Embodiment 26: The agricultural machine of Embodiment 25, wherein the at least one sensing circuit comprises a plurality of sensing circuits, and wherein each sensing circuit of the plurality is configured to selectively detect power provided to individual sensing electrodes of the plurality by the signal driver.

Embodiment 27: The agricultural machine of Embodiment 25, wherein the transmitter assembly further comprises an output driver configured to control voltages applied to of each of the plurality of sensing electrodes.

Embodiment 28: The agricultural machine of any one of Embodiment 1 through Embodiment 27, wherein the vehicle frame comprises a baler.

Embodiment 29: The agricultural machine of Embodiment 28, wherein the sensor is arranged such that hay traveling through the baler passes adjacent the at least one sensing electrode and the at least one guard electrode.

Embodiment 30: The agricultural machine of any one of Embodiment 1 through Embodiment 27, wherein the vehicle frame comprises a windrower, wherein the sensor is arranged such that the sensing electrode and the at least one guard electrode pass crop material as the windrower travels through a field.

Embodiment 31: A method comprising broadcasting a first electric field from a sensing electrode into a volume containing crop material, broadcasting a second electric field from at least one guard electrode adjacent the sensing electrode, measuring an attribute related to the first electric field, and correlating the measured attribute related to the first electric field to a property of the crop material in the volume. At least some field lines of the first electric field emanate from the sensing electrode through the volume. The presence of the second electric field changes a shape of the field lines of the first electric field.

Embodiment 32: The method of Embodiment 31, where the measured attribute comprises an attribute selected from the group consisting of current, power, voltage, reactance, impedance, resonance, capacitance, frequency, permittivity, and time.

Embodiment 33: The method of Embodiment 31 or Embodiment 32, wherein broadcasting a first electric field comprises applying a first voltage to the sensing electrode, and wherein broadcasting a second electric field comprises applying the first voltage to the at least one guard electrode.

Embodiment 34: The method of Embodiment 33, further comprising electrically isolating the sensing electrode from the at least one guard electrode.

Embodiment 35: The method of any one of Embodiment 31 through Embodiment 34, further comprising modifying an operating parameter of an agricultural machine based on the property of crop material in the volume.

Embodiment 36: A non-transitory computer-readable storage medium, the computer-readable storage medium including instructions that when executed by a computer, cause the computer to perform the method of any one of Embodiment 31 through Embodiment 35.

Embodiment 37: A capacitive sensor, comprising a transmitter assembly comprising a signal driver, at least one guard driver, and at least one sensing circuit configured to detect an output of the signal driver; at least one sensing electrode powered by the signal driver; and at least one guard electrode powered by the at least one guard driver. The at least one guard electrode is oriented such that a first electric field emanating from the at least one sensing electrode is shaped at least in part by a second electric field emanating from at least one the guard electrode.

Embodiment 38: The sensor of Embodiment 37, further comprising a cable comprising a first conductor connecting the at least one sensing circuit to the at least one sensing electrode and a second conductor connecting the at least one guard driver to the at least one guard electrode.

Embodiment 39: The sensor of Embodiment 38, wherein the cable comprises a coaxial cable.

Embodiment 40: The sensor of Embodiment 39, wherein the first conductor comprises an inner conductor of the coaxial cable and connects the sensing circuit to the at least one sensing electrode, and wherein the second conductor comprises an outer conductor of the coaxial cable and connects the guard driver to the at least one guard electrode.

Embodiment 41: The sensor of Embodiment 37, further comprising at least one ground electrode.

Embodiment 42: The sensor of Embodiment 41, wherein at least a portion of the at least one ground electrode is separated from and coplanar to the at least one sensing electrode.

Embodiment 43: The sensor of Embodiment 41 or Embodiment 42, wherein the at least one ground electrode laterally surrounds the at least one sensing electrode.

Embodiment 44: The sensor of any one of Embodiment 41 through Embodiment 43, wherein the at least one ground electrode shields the transmitter assembly.

Embodiment 45: The sensor of any one of Embodiment 41 through Embodiment 44, further comprising a cable comprising a first conductor connecting the at least one sensing circuit to the at least one sensing electrode, a second conductor connecting the at least one guard driver to the at least one guard electrode, and a third conductor connecting the at least one ground electrode to a ground of the transmitter assembly.

Embodiment 46: The sensor of Embodiment 45, wherein the cable comprises a triaxial cable.

Embodiment 47: The sensor of any one of Embodiment 41 through Embodiment 46, wherein field lines emanating from the at least one sensing electrode intersect the at least one ground electrode.

Embodiment 48: The sensor of any one of Embodiment 37 through Embodiment 47, wherein field lines emanating from a major rear surface of the at least one sensing electrode are spaced more densely than field lines emanating from a major front surface of the at least one sensing electrode.

Embodiment 49: The sensor of any one of Embodiment 37 through Embodiment 48, wherein the transmitter assembly is configured to provide a first voltage to the at least one sensing electrode and a second voltage to the at least one guard electrode, wherein the first voltage and the second voltage are identical in magnitude but electrically isolated.

Embodiment 50: The sensor of any one of Embodiment 37 through Embodiment 48, wherein the transmitter assembly is configured to provide a first voltage to the at least one sensing electrode and a second voltage to the at least one guard electrode, wherein the second voltage is offset from the first voltage by a preselected amount.

Embodiment 51: The sensor of any one of Embodiment 37 through Embodiment 50, wherein the at least one guard electrode shields the transmitter assembly.

Embodiment 52: The sensor of any one of Embodiment 37 through Embodiment 51, wherein the signal driver and the at least one guard driver share a common power source.

Embodiment 53: The sensor of any one of Embodiment 37 through Embodiment 52, wherein a major rear surface of the at least one sensing electrode is adjacent a major front surface of the at least one guard electrode.

Embodiment 54: The sensor of Embodiment 53, wherein a shortest path from any point on the major rear surface of the at least one sensing electrode outward intersects the major front surface of the at least one guard electrode before reaching any other object.

Embodiment 55: The sensor of any one of Embodiment 37 through Embodiment 52, wherein a major front surface of the at least one sensing electrode is coplanar with a major front surface of the at least one guard electrode.

Embodiment 56: The sensor of any one of Embodiment 37 through Embodiment 55, wherein the at least one guard electrode comprises a plurality of guard electrodes.

Embodiment 57: The sensor of Embodiment 56, wherein the transmitter further comprises a multiplexor configured to selectively provide power from the at least one guard driver to individual guard electrodes of the plurality.

Embodiment 58: The sensor of Embodiment 57, further comprising a controller configured to drive the multiplexor.

Embodiment 59: The sensor of Embodiment 56, wherein the at least one guard driver comprises a plurality of switched guard drivers, and wherein each switched guard driver of the plurality is configured to selectively provide power to individual guard electrodes of the plurality.

Embodiment 60: The sensor of Embodiment 59, wherein the transmitter assembly further comprises a controller configured to drive the plurality of switched guard drivers.

Embodiment 61: The sensor of any one of Embodiment 37 through Embodiment 60, wherein the at least one sensing electrode comprises a plurality of sensing electrodes.

Embodiment 62: The sensor of Embodiment 61, wherein the at least one sensing circuit comprises a plurality of sensing circuits, and wherein each sensing circuit of the plurality is configured to selectively detect power provided to individual sensing electrodes of the plurality by the signal driver.

Embodiment 63: The sensor of Embodiment 61, wherein the transmitter assembly further comprises an output driver configured to control voltages applied to of each of the plurality of sensing electrodes.

Embodiment 64: A method comprising broadcasting a first electric field from a sensing electrode into a volume, broadcasting a second electric field from at least one guard electrode adjacent the sensing electrode, measuring an attribute related to the first electric field, and correlating the measured attribute related to the first electric field to a property of material in the volume. At least some field lines of the first electric field emanate from the sensing electrode through the volume. The presence of the second electric field changes a shape of the field lines of the first electric field.

Embodiment 65: The method of Embodiment 64, where the measured attribute comprises an attribute selected from the group consisting of current, power, voltage, reactance, impedance, resonance, capacitance, frequency, permittivity, and time.

Embodiment 66: The method of Embodiment 64 or Embodiment 65, wherein broadcasting a first electric field comprises applying a first voltage to the sensing electrode, and wherein broadcasting a second electric field comprises applying the first voltage to the at least one guard electrode.

Embodiment 67: The method of Embodiment 66, further comprising electrically isolating the sensing electrode from the at least one guard electrode.

Embodiment 68: The method of any one of Embodiment 64 through Embodiment 67, further comprising modifying an operating parameter of a machine based on the property of material in the volume.

Embodiment 69: A non-transitory computer-readable storage medium, the computer-readable storage medium including instructions that when executed by a computer, cause the computer to perform the method of any one of Embodiment 64 through Embodiment 68.

All references cited herein are incorporated herein in their entireties. If there is a conflict between definitions herein and in an incorporated reference, the definition herein shall control.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the invention as hereinafter claimed, including legal equivalents thereof. In addition, features from one embodiment may be combined with features of another embodiment while still being encompassed within the scope of the invention as contemplated by the inventors. Further, embodiments of the disclosure have utility with different and various crop-harvesting machine types and configurations.

What is claimed is:

1. An agricultural machine, comprising:
   a vehicle frame; and
   a capacitive sensor carried by the vehicle frame, the capacitive sensor comprising:
      a transmitter assembly comprising a signal driver, at least one guard driver, and at least one sensing circuit configured to detect an output of the signal driver;
      at least one sensing electrode powered by the signal driver; and
      a plurality of guard electrodes powered by the at least one guard driver;
   wherein the guard electrodes are oriented such that a first electric field emanating from the at least one sensing electrode is shaped at least in part by a second electric field emanating from at least one guard electrode of the plurality of guard electrodes.

2. The agricultural machine of claim 1, further comprising at least one ground electrode.

3. The agricultural machine of claim 2, wherein at least a portion of the at least one ground electrode is separated from and coplanar to the at least one sensing electrode.

4. The agricultural machine of claim 2, wherein the at least one ground electrode laterally surrounds the at least one sensing electrode.

5. The agricultural machine of claim 2, wherein the at least one ground electrode shields the transmitter assembly.

6. The agricultural machine of claim 2, wherein the sensor further comprises a cable comprising:
   a first conductor connecting the at least one sensing circuit to the at least one sensing electrode;
   a second conductor connecting the at least one guard driver to the guard electrodes; and
   a third conductor connecting the at least one ground electrode to a ground of the transmitter assembly.

7. The agricultural machine of claim 2, wherein field lines emanating from the at least one sensing electrode intersect the at least one ground electrode.

8. The agricultural machine of claim 1, wherein the transmitter assembly is configured to provide a first voltage to the at least one sensing electrode and a second voltage to at least one guard electrode of the plurality of guard electrodes, wherein the first voltage and the second voltage are identical in magnitude but electrically isolated from one another.

9. The agricultural machine of claim 1, wherein the transmitter assembly is configured to provide a first voltage to the at least one sensing electrode and a second voltage to at least one guard electrode of the plurality of guard electrodes, wherein the second voltage is offset from the first voltage by a preselected amount.

10. The agricultural machine of claim 1, wherein a major rear surface of the at least one sensing electrode is adjacent a major front surface of at least one guard electrode of the plurality of guard electrodes.

11. The agricultural machine of claim 1, wherein a major front surface of the at least one sensing electrode is coplanar with a major front surface of at least one guard electrode of the plurality of guard electrodes.

12. The agricultural machine of claim 1, wherein the transmitter further comprises a multiplexor configured to selectively provide power from the at least one guard driver to individual guard electrodes of the plurality of guard electrodes.

13. The agricultural machine of claim 1, wherein the at least one guard driver comprises a plurality of switched guard drivers, and wherein each switched guard driver is configured to selectively provide power to an individual guard electrode.

14. The agricultural machine of claim 1, wherein the at least one sensing electrode comprises a plurality of sensing electrodes, wherein the at least one sensing circuit comprises a plurality of sensing circuits, and wherein each sensing circuit is configured to selectively detect power provided to individual sensing electrodes by the signal driver.

15. The agricultural machine of claim 1, wherein the vehicle frame comprises a baler, wherein the sensor is arranged such that hay traveling through the baler passes adjacent the at least one sensing electrode and the plurality of guard electrodes.

16. The agricultural machine of claim 1, wherein the vehicle frame comprises a windrower, and wherein the sensor is arranged such that the sensing electrode and the plurality of guard electrodes pass crop material as the windrower travels through a field.

17. The agricultural machine of claim 1, wherein the at least one guard driver is configured to selectively power each of the plurality of guard electrodes.

18. A method comprising:
   broadcasting a first electric field from a sensing electrode into a volume containing crop material, wherein at least some field lines of the first electric field emanate from the sensing electrode through the volume;
   broadcasting a second electric field from at least one guard electrode of a plurality of guard electrodes adjacent the sensing electrode, wherein the presence of the second electric field changes a shape of the field lines of the first electric field;
   measuring an attribute related to the first electric field; and
   correlating the measured attribute related to the first electric field to an amount or distribution of the crop material in the volume.

19. The method of claim 18, where the measured attribute comprises an attribute selected from the group consisting of current, power, voltage, reactance, impedance, resonance, capacitance, frequency, permittivity, and time.

20. The method of claim 18, wherein broadcasting a first electric field comprises applying a first voltage to the sensing electrode, and wherein broadcasting a second electric field comprises applying the first voltage to the at least one guard electrode.

21. The method of claim 18, further comprising modifying an operating parameter of an agricultural machine based on the amount or distribution of crop material in the volume.

22. The method of claim 18, where the amount or distribution of the crop material in the volume comprises an amount or distribution selected from the group consisting of total crop volume, crop density, lateral distribution, crop depth, and distance from the sensing electrode to the crop material.

23. A non-transitory computer-readable storage medium, the computer-readable storage medium including instructions that when executed by a computer, cause the computer to perform the method of claim 18.

\* \* \* \* \*